United States Patent [19]

Kwan et al.

[11] Patent Number: 4,772,325

[45] Date of Patent: Sep. 20, 1988

[54] FLUORINE-CONTAINING DENTAL MATERIALS

[75] Inventors: Stephen C. Kwan, Arlington, Tex.; John J. O'Connell, Tustin, Calif.

[73] Assignee: Kerr Manufacturing Company, Romulus, Mich.

[21] Appl. No.: 44,206

[22] Filed: Apr. 30, 1987

Related U.S. Application Data

[60] Division of Ser. No. 476,563, Mar. 18, 1983, abandoned, which is a continuation of Ser. No. 269,129, Jun. 1, 1981, abandoned.

[51] Int. Cl.⁴ .................... A61C 5/00; C09K 3/00
[52] U.S. Cl. .................... 106/35; 528/91; 433/215; 433/218; 433/219
[58] Field of Search .................... 166/35; 528/91; 433/215, 218, 219

[56] References Cited

U.S. PATENT DOCUMENTS

| | | | |
|---|---|---|---|
| 2,717,885 | 9/1955 | Greenlee | 528/91 |
| 2,824,083 | 2/1958 | Parry et al. | 528/91 |
| 2,980,733 | 4/1961 | Sowa | 424/52 |
| 3,327,016 | 6/1967 | Lee | 106/35 |
| 3,793,247 | 2/1974 | Latto et al. | 528/91 |
| 3,799,905 | 3/1974 | Holloway et al. | 528/91 |

FOREIGN PATENT DOCUMENTS

827699 2/1960 United Kingdom.

OTHER PUBLICATIONS

*Scandinavian Journal of Dental Research* (1972) 80, pp. 515-519, "Fluoride Release by Silicate Cements and Composite Resins", by Forsten and Paunio.

*Primary Examiner*—Theodore Morris
*Attorney, Agent, or Firm*—Marjama & Pincelli

[57] ABSTRACT

This invention relates to a fluorine-containing dental composition. The composition is particularly adapted for use in the field of dentistry as a composite filling material, cavity liner, adhesive, orthodontic resin, pit and fissure sealant, and denture base material wherein the fluoride is released to prevent secondary caries and reduce plaque formation.

6 Claims, No Drawings

FLUORINE-CONTAINING DENTAL MATERIALS

This is a division of application Ser. No. 476,563 filed Mar. 18, 1983 which is a continuation of Ser. No. 269,129, filed June 1, 1981, both now abandoned.

BACKGROUND OF THE INVENTION

It is established that dental silicate cements containing fluoride are therapeutic in preventing secondary caries and reducing plaque formation. Present acrylic denture base material, restorative materials and adhesives have been shown to be sites of bacterial and plaque accumulation, which can be a precursor of irritation to soft tissues and caries attack on remaining natural dentition. The release of fluoride ion from these dental restorative materials occurs either by surface release, or by dissolution of the fluorine-containing additives or the dental restorative material itself with consequent migration of fluoride ions into the underlying tooth structure. Various fluorine-containing additives that have been tried in dental restorations consist of inorganic fluroide salts, organic bases such as amine hydrofluoride, fluorocarbons and fluoride-containing ion-exchange resins. These attempts to find suitable fluoride-containing additives which are both dispersed in dental restorative material and capable of reducing tooth caries through controlled long-term fluoride release have failed. Silicate cements have demonstrated cariostatic release of fluoride; however, the strictly rapid surface release of fluoride from the cement, the dissolution of the cement in oral fluids, and the low tensile strengths of the cements are major disadvantages. Alternatively, the fluroide incorporated into insoluble resin materials has been considered to be virtually incapable of leaking out, and thus to be ineffective as a cariostatic agent. Studies by Forsten and Paunio (*Scandinavian Journal of Dental Research* (1972) 80, 515–519) comparing fluoride release by silicate cements and composite resins have shown that the overall release of fluoride from the two materials was comparable; however, the manner in which the fluoride was released from the composite was not controlled. Heretofore it was difficult to obtain controlled, effective cariostatic and plaque-reducing fluoride release from virtually insoluble materials such as acrylic denture base materials, adhesives and composite resins, and the like.

SUMMARY OF THE INVENTION

In accordance with the present invention, we have discovered a controlled, slow fluoride releasing additive comprising a Lewis base and a fluoride-containing Lewis acid which is therapeutic in preventing secondary caries and reducing plaque formation. This additive is incorporated into polymeric dental restorative material and is capable of migrating from the interior to the surface of said material without dissolution thereof and with consequent release of fluoride.

DETAILED DESCRIPTION OF THE INVENTION

We have now found that Lewis acid compounds containing covalently bound fluoride can be reacted with Lewis base compounds to produce addition compounds which are mixed with dental restorative materials and release fluoride ion. The flouride is released at a controlled rate by diffusion of the Lewis acid within said dental material with subsequent hydrolysis upon contact with water. The fluorine-containing Lewis acid—Lewis base addition compounds of the present invention can be added to dental restorative materials, denture base materials, orthodontic elastics, plastic dental materials, and dental resins. Alternatively, the addition compounds can be incorporated into the polymer matrix as part of the monomer resin constituents. The principal requirements of these compounds are that the Lewis base compounds are dispersible or soluble within the dental restorative material; the Lewis acid compound must be mobile within the restorative material and capable of migrating to the surface of said material to release fluoride ion by dissociation with water at a controlled rate; and the resulting Lewis acid—Lewis base addition compound and its hydrolysis products must be non-toxic.

The Lewis acid compounds used in this invention may be any covalently bound fluorine-containing compound with a vacant electron orbital which can be used to form a covalent bond with the electron pair of a base, yet which retains its mobility within the dental restorative material. Examples of fluorine-containing Lewis acid compounds are aluminum trifluoride, boron trifluoride, gallium trifluoride, titanium tetrafluoride and indium trifluoride. We have found that boron trifluoride works well in accordance with the present invention; thus it is the preferred fluorine-containing Lewis acid compound.

Lewis base compounds in accordance with the present invention may be any compound having an available pair of electrons, either unshared or in a $\pi$-electron orbital, which is dispersible or soluble within the dental restorative material. The Lewis base compounds in accordance with this invention are primary amines having the formula $H_2N(R_1)$, secondary amines having the formula $HN(R_1)_2$, tertiary amines having the formula $N(R_1)_3$, ethers having the formula $R_1OR_1$, esters having the formula $R_1COOR_1$, ketones having the formula $R_1COR_1$, alcohols having the formula $R_1OH$, mercaptans, thioethers and thioesters, wherein $R_1$ is a hydroxyl, a substituted or unsubstituted aromatic group, or a linear or branched, saturated or unsaturated, substituted or unsubstituted aliphatic group, wherein the carbon chain length of these aliphatic groups is limited to the number of carbon atoms which produce a compound which is dispersible or soluble within a dental restorative material. A preferred chain length of the aliphatic group is from about 1 to about 18 carbon atoms. We have found that aliphatic chains containing from about 1 to about 12 carbon atoms operate most successfully in accordance with this invention, and are thus most preferred.

Examples of Lewis base compounds in accordance with the present invention are: butylamine, octylamine, dodecylamine, aniline, isobutyl amine, isooctylamine, isopropylamine, glycine, alanine, valine, hydroxylamine, tryptophan, aspartic acid, n-amino-1-butene, n-amino-2-octene, ethanolamine, octanolamine, dodecanolamine, 3-methoxyaniline, dimethylamine, dibutylamine, dioctylamine, didodecylamine, methylethylamine, methylbutylamine, butyloctylamine, octyldodecylamine, methylhydroxylamine, butylethanolamine, octyldodecanolamine, methylisobutylamine, ethylisooctylamine, butylisopropylamine, N-methylaniline, N-methyl-3-methoxyaniline, trimethylamine, triethylamine, trioctylamine, tridodecylamine, dimethyloctylamine, dibutyldodecylamine, triisobutylamine, triisoctylamine, triisopropylamine, dimethylisobutylamine, dibutylisooctylamine, tributeneamine, triethanolamine, triisopropanolamine, triphenylamine, methyldiphenylamine, octyldiphenylamine, pyridine, dimethylether, dibutylether, didodecylether, methylethylether, diiso:butylether, disopropylether, methylisobutylether, butylisoctylether, octylisododecylether, diphenylether and ethyl acetate. A preferred Lewis base compound in accordance with this invention is triethylamine.

Additional Lewis base compounds in accordance with the present invention are aminoalkyls. The preferred Lewis base compounds in accordance with this invention are diamines having the formula:

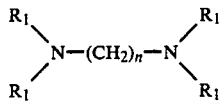

wherein $R_1$ is a substituted or unsubstituted aromatic group, a hydroxyl group, hydrogen, or a linear or branched, saturated or unsaturated, substituted or unsubstituted aliphatic group having from about 1 to about 12 carbon atoms, and n is an integer having from about 1 to about 9 carbon atoms. The chain length of the alkylene group is limited to the number of carbon atoms which produce a compound which is dispersible or soluble within a dental restorative material. We have found that compounds having alkylene chains containing from about 1 to about 9 carbon atoms are preferred in accordance with this invention. Examples of diamines in accordance with the present invention are: N,N,N',N'-tetramethylethylenedimine, N,N,N',N'-tetraoctylbutylenediamine, N,N,N',N'-tetraisobutyloctylenediamine, N,N,N',N'-tetraphyntylethylenediamine, and N,N-dihydroxy-N',N'-diphenylethylenediamine. The preferred compound of the present invention is N,N,N'N'-tetramethylethylenediamine.

In an alternative embodiment of this invention, the Lewis base components can be monomer resin constituents capable of becoming incorporated into the backbone, side chain, or crosslink of the polymeric dental material. In accordance with this invention, examples of monomer resin constituents include compounds having the formula:

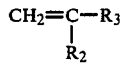

wherein $R_2$ is hydrogen, or a cyano, or a substituted or unsubstituted aromatic group, or a linear or branched, substituted or unsubstituted, saturated or unsaturated alkyl; and $R_3$ is an esterified carboxyl, a primary amine, a secondary amine, a tertiary amine, a carboxyl amine as illustrated by acrylamide ($CH_2CHCONH_2$), or an amine-containing ester having the formula:

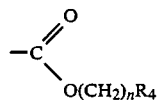

wherein $R_4$ is a primary amine, a secondary amine, or a tertiary amine, and n is an integer representing from about 1 to about 18 and preferably from about 1 to 9 carbon atoms. Examples of monomer resin constituents in accordance with the present invention are: acrylic and methacrylic esters such as methylacrylate, ethylacrylate, propylacrylate, butylacrylate, 2-ethoxyhexylacrylate, methylmethacrylate, ethylmethacrylate, propylmethacrylate, butylmethacrylate, lauryl-methacrylate, stearylmethacrylate, ethylisobutylacrylate, butylenedimethacrylate, and trimethylolpropane trimethacrylate; acrylonitrile; trimethylaminostyrene; polyamides such as acrylamide and methacrylamide; polycyclamide constituents such as 1,4-cyclohexane bis (methylamine); amion resins such as carbamide, melamine, thiocarbamide, aniline, dicyanodiamide, toluenesulfonamide, benzoguanamine, ethylene urea; urethanes, epoxies, polyesters, polycarbonates, and isocyanate derivatives such as toluene diisocyanate and diphenyl methane diisocyanate. A preferred Lewis base monomer resin component of this invention is diethylaminoethylmethacrylate (DEAEMA).

In accordance with the present invention, the fluorine-containing Lewis acid—Lewis bae compounds are added to restorative dental materials or are incorporated into polymer-based dental restorative materials as constituent resin components. In either case, the content of the fluorine-containing compound within the dental material should be limited so as not to interfere with the physical properties of the material. In addition, the content of the fluorine-containing compound should be high enough to effectively release fluoride ion and reduce tooth caries in a controlled sustained manner over a long period of time. Compositions containing up to about 50 wt % of the fluorine-containing Lewis acid—Lewis base addition compound, do not adversely affect the physical properties of the dental materials and operate effectively in a controlled, slow-fluoride release composite, Thus, compositions having from about 0.5 to about 50 wt % of the fluorine-containing compounds are preferred in this invention. Concentrations as low as 0.05% wt flouride compounds can be effective in preventive dentistry. A more preferred range of compositions is from about 0.5 to about 25 wt % of the fluorine-containing compound. The most preferred compositions in accordance with this invention contain from about 0.5 to about 1.5 wt % of the fluorine-containing addition compounds. It should be noted, however, that the various dental materials used in accordance with this invention will exhibit different physical characteristics when their respective formulations are modified, so that the quantity of the fluoride-containing compounds of this invention must be evaluated with each formulation.

The dental restorative materials used in accordance with this invention include resin cements, dental prosthetic devices, denture base resins, cavity liners, composite resins, pit and fissure sealants, resin adhesives, repair materials, relining and rebasing dental materials, orthodontic resins, orthodontic elastics, plastic orthodontic brackets, or any other such material used in restorative dental operations. Presently employed dental restorative materials are fabricated from polymer-based materials, metals, ceramics, or combinations (composite) thereof. Examples of polymer-based materials in accordance with this invention include acrylic and methacrylic polymers, vinyl acrylic polymers, cyanoacrylates, polystyrene, polycarbonate, epoxy resins, nylons, vinyl styrenes, unsaturated polyesters, polyurethane, polyvinylacetate-ethylene, silicones, polyvinylchloride, copolymer formualtions using these polymers, or modifications thereof which prove useful as dental materials. Examples of dental composites in accordance with this invention include glass ionomer cements, acrylic composite restorative filling materials, Bis-GMA resin composites, acrylic restorative tooth lines, and urethane dimethacrylate composites. A discussion of dental restorative materials and their composition, application, and properties can be found in *Restorative Dental Materials*, by Robert G. Craig, published by the C.V. Mosby Publishing Company, 1980, incorporated herein by reference. Preferred dental restorative materials in accordance with the present invention include restorative composite resins, cavity liners, adhesives, pit and fissure sealants, orthodontic resins, and denture base materials. The most preferred dental restorative materials are cavity liners, adhesives, sealants and denture base materials.

The following examples describe certain representative embodiments of this invention as set forth above. They are to be illustrative only and are not intended to limit the scope of the invention

EXAMPLE 1

The following example describes the preparation and chemical characterization of the fluorine-containing Lewis acid—Lewis base compounds of the present invention and their use in dental restorative materials.

A quantity of 25 gm diethylaminoethylmethacrylate (DEAEMA) are placed in a three-neck round-bottom flask. The flask is set into an ice bath to moderate reaction temperature. A vacuum is drawn on the reaction flask and gaseous boron trifluoride is bubbled into the DEAEMA at such a rate that the temperature does not exceed 35° C. The rate of bubbling is increased when the temperature begins to fall. The reaction is continued until the temperature no longer increases on increased boron trifluoride addition. This takes about one hour, when the reaction product is collected and then purified by distillation using a molecular still. The product prepared accordingly was determined to be the 1:1 adduct of DEAEMA and boron trifluoride (DEAEMA-BF$_3$) on the basis of infrared spectroscopy, thermogravimetric analysis, nuclear magnetic resonance spectroscopy and elemental analysis. The corresponding structure is shown below:

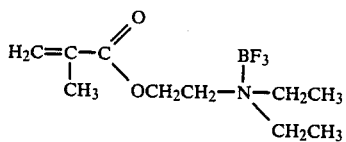

This material (DEAEMA-BF) was used in combination with other methacrylate monomers to prepare a formulation suitable for composite restorative liner preparations according to the formulation below:
35 parts Bis-GMA (reaction product of methacrylic acid and the diglycidyl ether of bisphenol A)
30 parts ethyleneglycoldimethacrylate
30 parts trimethylolpropanetrimethacrylate
5 parts DEAEMA-BF$_3$
1 part dihydroxyethyl-para-tolylamine The above material is polymerized by mixing 5 parts with 1 part of saturated (9%) benzoyl peroxide solution in dimethylphthalate. 0.1 gm samples of hardened material were stored in 10 ml of distilled water. The fluoride content was measured periodically with an ion-specific electrode, and significant levels of fluoride were still being released after more than three months.

Additionally, the fluoride leach (ppm/day) was determined based upon a 0.01 gm application of the composite in contact with 0.1 ml of water. For comparison, identical tests were run of films of a silico phosphate cement (Fluorothin) and a silicate cement (MQ). The results indicate that the experimental composite liner maintained a detectable release of fluoride over a longer period of time than the silicate cements, even though the silicate cements release larger amounts of fluoride during the initial part of the leach.

EXAMPLE 2

The following example describes an alternate method of preparing the fluorine-containing Lewis acid—Lewis base compounds of the present invention.

A quantity of 37 gm of diethylaminoethylmethacrylate (DEAEMA) are placed in a three-neck round-bottom flask. Gaseous oxygen is bubbled in for one-half hour. After the oxygen flow is shut off, 26 gm of boron trifluoride methanol complex is placed in a dropping funnel. The funnel is mounted on top of the round-bottom flask in an ice water bath. The temperature is cooled to about 10° C. The boron trifluoride methanol is added dropwise while the mixture is stirred. Temperature is maintained between 15°-25° C. by adjustment of addition of the boron trifluoride methanol material. Complete addition requires 20 to 30 minutes. Next, the oxygen flow is resumed to bubble off methanol and unreacted materials. After four hours material is collected and weighed. The yield is 49 gm.

EXAMPLE 3

The following example describes the preparation and physical properties of a dental adhesive in accordance with this invention.

The DEAEMA-BF$_3$ compound was prepared as in Example 1. This material was used in combination with other methacrylate monomers to prepare a formulation suitable for orthodontic adhesive preparations. Equal amounts of solutions A and B, described below, are mixed together to form the desired adhesive:
Solution A
14 parts DEAEMA-BF$_3$
28 parts diethyleneglycoldimethacrylate
29 parts Bis-GMA
27 parts fumed silica
2 parts dihydroxyethyl-para-tolylamine Solution B
42 parts diethyleneglycoldimethacrylate
29 Bis-GMA
27 parts fumed silica
1 part benzoyl peroxide

Fluoride Release

Cured discs of material measuring 0.015 to 0.050 inches thick and 1.5 inches in diameter were immersed in 50 ml portions of distilled water. The fluoride concentration of the exposed water was determined at measured intervals using a fluoride-specific ion electrode. After each determination, the water was discarded and replaced with an additional portion of distilled water. Rates of release have been determined to be 2 to 5 micrograms of fluoride per square centimeter per day. The samples thus studied have fluoride available for release for over one year.

EXAMPLE 4

The DEAEMA-BF$_3$ adduct is prepared according to Example 1, and is used in combination with other methacrylate monomers to prepare a formulation suitable for denture-base preparations according to the following composition: The liquid resin portion of a powder or liquid denture-base material is formulated by mixing 1 part of a solution containing 4 parts DEAEMA-BF$_3$ and 6 parts methylemthacrylate containing 2% dimethyl-para-toluidine and 2 parts commercial denture-base powder (polymethylmethacrylate) to form test specimens and acrylic dental devices.

EXAMPLE 5

The DEAEMA-BF$_3$ addition compound can be prepared according to Example 1 and used in combination with other methacrylate monomers to prepare a formulation suitable for pit and fissure sealant preparations according to the following composition: Equal amounts of solution A and solution B as described below can be mixed together to form a chemically cured pit and fissure sealant:

Solution A 20 parts DEAEMA-BF$_3$
40 parts diethyleneglycoldimethacrylate
40 parts Bis-GMA
2 parts dihydroxyethyl-para-tolylamine Solution B 60 parts diethyleneglycoldimethacrylate
40 parts Bis-GMA
1 part benzoyl peroxide

EXAMPLE 6

The DEAEMA-BF$_3$ addition compound was prepared as shown in Example 1 and used in combination with other methacrylate monomers to prepare a formulation suitable for composite restorative liner preparations according to the following composition:
35 parts Bis-GMA
30 parts ethyleneglycoldimethacrylate
30 parts trimethylolpropanetrimethacrylate
2.5 parts DEAEMA-BF$_3$
1 part dihydroxyethyl-para-tolylamine The above material is polymerized by mixing 5 parts with 1 part of saturated 9% benzoyl peroxide solution in dimethylphthalate. 0.1 gm samples of hardened material were stored in 10 ml of distilled water. the fluoride content was measured periodically with an ion-specific electrode and significant levels of fluoride were still being released after more than three months. For comparison, identical tests were run of films of fluorothin, a silica phosphate cement, and MQ, a silicate cement. Results indicate that the experimental composite films maintained a detectable release of fluoride over a longer period of time than the fluorothin and MQ films, even though the silica phosphate and silicate cements released larger amounts of fluoride during the initial part of the leach.

EXAMPLE 7

A quantity 15 gm N,N,N',N'-tetramethylethylenediamine (TMED) are placed in a three-neck round-bottom flask. The flask is set into an ice bath to moderate reaction temperature. A vacuum is drawn on the reaction flask and gaseous boron trifluoride is bubbled at such a rate that the temperature does not exceed 35° C. The rate of bubbling is increased when the temperature begins to fall. The reaction is continued until the temperature no longer increases on increased boron trifluoride addition. This takes about one hour when the reaction product is collected and then purified by distillation using a molecular still.

The resulting addition compound is used in combination with methacrylate monomers to prepare a formulation suitable for composite resin filing materials according to the formulation below:
13 parts Bis-GMA
3 parts trimethylolpropanetrimethacrylate
3 parts ethyleneglycoldimethacrylate
0.01 parts 2,6-di-t-butyl-p-cresol
0.2 parts N,N, diethanol-m-tolylamine
1 part permasorb MA
17 parts Calcium silicate
0.04 parts Tilanium dioxide
60 parts Barium silicate
3 parts TMED BF$_3$

EXAMPLE 8

The DEAEMA-BF$_3$ compound was prepared as shown in Example 1. This compound was then added to an experimental formulation of a composite restorative liner as shown below:
35 parts Bis-GMA
30 parts ethyleneglycoldimethacrylate
30 parts trimethylolpropanetrimethacrylate
5 parts DEAEMA-BF$_3$
0.84 pphr N,N-diethanol-p-tolylamine
0.05 pphr 2,6 di-t-butyl-p-cresol
2.5 pphr benzophenone Results of tests show that the thermal and ultraviolet color stability of these liners are good, as is their compatibility with silicate cements and composite resins.

EXAMPLE 9

A composite restorative liner was prepared as shown in Example 6. Analysis of leaching of the fluorine-containing Lewis acid—Lewis base addition compound indicates that the boron content of the restorative liner leaching solution is much less than it should be if all the available boron is leached.

| Solution (% Adduct) | Leach Sol'n Fluoride Content | % Total Avail. Fluoride Leached | Avail. Boron* | Exp. Boron in Leach Sol'n | % of Boron Avail. |
| --- | --- | --- | --- | --- | --- |
| (5%) | 12 μg | 22.5 | 40 μg | 7.4 μg | 18.5% |
| (2.5%) | 8.4 μg | 32 | 29 μg | 2.6 μg | 8.8%* |

*Based upon measured fluoride content in leach solution.

To measure the fluoride-releasing characteristics of cured experimental restorative liners, 0.1 gm films of 9 to 13 mils thickness were soaked for an extended period in 10 mls water. Fluoride ion concentrations were measured periodically, using an ion-specific electrode.

We claim:
1. A method of treating teeth with a dental composition which comprises a polymer based material selected from the group consisting of acrylics, methacrylics, urethanes, vinyls, silicones, and copolymers and modifications thereof, which further contains a controlled fluoride release compound which is effective in preventive dentistry, wherein said controlled fluoride release compound comprises a complex of a Lewis base and boron trifluoride which is dispersible or soluble in said dental composition; said release compound being present in a concentration of about 0.05 to 50 weight percent of said dental composition, with said dental composition being placed in direct contact with one or more teeth and being in the form of at least one member selected from the group consisting of restorative composite resins, cavity liners, resin adhesives, pit and fissure sealants, orthodontic resins, orthodontic elastics, and plastic orthodontic brackets.

2. The method of claim 1 wherein the Lewis base is at least one member selected from the group consisting of amines, ethers, esters, acids, ketones, alcohols, mercaptans, thioethers and thioesters.

3. The method of claim 1 wherein in the structure of the Lewis base is an amine represented by the formula:

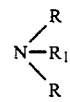

wherein R and $R_1$ are hydrogen, a hydroxyl, a substituted or unsubstituted aromatic group, or a linear or branched, saturated or unsaturated, substituted or unsubstituted aliphatic group.

4. The method of claim 1 wherein the Lewis base is a constituent resin component of the polymeric dental composition.

5. The method of claim 1 in which the concentration of controlled fluoride release compound comprises about 0.5 to 25 weight percent of the dental composition.

6. The method of claim 1 in which the concentration of controlled fluoride release compound comprises about 0.5 to 1.5 weight percent of the dental composition.

* * * * *